United States Patent [19]

Fukuoka et al.

[11] Patent Number: 5,072,007
[45] Date of Patent: Dec. 10, 1991

[54] PROCESS FOR PREPARING POLYALKYL-2-ALKOXY-7-HYDROXY-CHROMAN DERIVATIVES

[75] Inventors: Daisuke Fukuoka; Takeshi Ishitoku; Katsuya Takahashi; Takashi Tashiro; Junichi Imuta; Hiroaki Tan; Masaharu Ishiguro; Noriaki Kihara; Teruaki Mukaiyama, all of Yamaguchi, Japan

[73] Assignee: Mitsui Petrochemical Industries, Ltd., Tokyo, Japan

[21] Appl. No.: 547,132

[22] Filed: Jul. 3, 1990

[30] Foreign Application Priority Data

Jul. 3, 1989 [JP] Japan ................. 1-169947

[51] Int. Cl.$^5$ .................................. C07D 311/16
[52] U.S. Cl. .................................. 549/399
[58] Field of Search .......................... 549/399

[56] References Cited

U.S. PATENT DOCUMENTS 4,838,924  6/1989  Takematsu et al. ............... 71/88

*Primary Examiner*—Nicky Chan
*Attorney, Agent, or Firm*—Sherman and Shalloway

[57] ABSTRACT

Process for preparing polyalkyl-2-alkoxy-7-hydroxy-chroman derivative of the general formula (V):

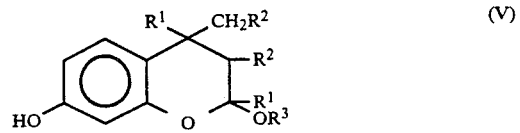

wherein $R^1$ denotes lower primary alkyl, $R^2$ denotes hydrogen or lower primary alkyl and $R^3$ denotes lower-alkyl, by reacting resorcin with either an aliphatic ketone of the general formula (I):

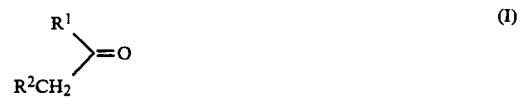

wherein $R^1$ and $R^2$ are as defined above, and an alcohol of the formula (II):

$$R^3OH \qquad (II)$$

wherein $R^3$ is as defined above, in the presence of an acid catalyst, or an aliphatic ketone acetal of the general formula (III):

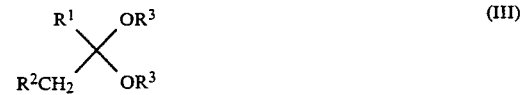

wherein $R^1$, $R^2$ and $R^3$ are as defined above, in the presence of an acid catalyst.

13 Claims, No Drawings

PROCESS FOR PREPARING POLYALKYL-2-ALKOXY-7-HYDROXYCHROMAN DERIVATIVES

FIELD OF THE INVENTION

The present invention relates to a novel process for preparing polyalkyl-2-alkoxy-7-hydroxychroman derivative of the general formula (V):

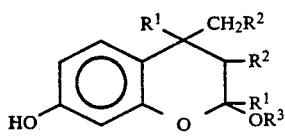

wherein $R^1$ denotes lower primary alkyl, $R^2$ denotes hydrogen or lower primary alkyl and $R^3$ denotes lower-alkyl.

The compounds of the formula (V) are useful as an intermediate for the preparation of agricultural chemicals.

PRIOR ART

Both the processes for preparing polyalkyl-2-alkoxy-7-hydroxychroman derivatives by reacting resorcin with an α,β-unsaturated ketone and an ortho-ester in the presence of an acid catalyst, and by reacting resorcin with an α,β-unsaturated aldehyde acetal in the presence of an acid catalyst have already been filed by the present inventors and laid open to public with Japanese Patent LOP-Publn. No. 203677/1988.

PROBLEMS TO BE SOLVED BY THE INVENTION

The processes disclosed in the aforementioned Japanese Patent LOP-Publn. No. 203677/1988 can produce the desired product in a single step and therefore are industrially advantageous.

However, those compounds having two alkyl substituents on the 4-carbon atom of the chroman ring could not be synthesized by the above described methods.

The inventors tried to solve the above problem by replacing the reactants α,β-unsaturated ketone and ortho-ester or α,β-unsaturated aldehyde acetal with other reactant (s).

SUMMARY OF THE INVENTION

Thus, the present invention relates to a process for preparing polyalkyl-2-alkoxy-7-hydroxychroman derivatives of the general formula (V):

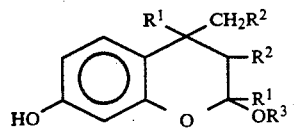

wherein $R^1$ denotes lower primary alkyl, $R^2$ denotes hydrogen or lower primary alkyl and $R^3$ denotes lower-alkyl, which comprises reacting resorcin with either an aliphatic ketone of the general formula (I):

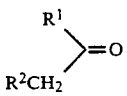

wherein $R^1$ and $R^2$ are as defined above, and an alcohol of the formula (II):

$$R^3OH \qquad (II)$$

wherein $R^3$ is as defined above, in the presence of an acid catalyst (Process 1), or an aliphatic ketone acetal of the general formula (III):

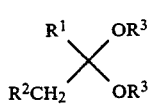

wherein $R^1$, $R^2$ and $R^3$ are as defined above, in the presence of an acid catalyst (Process 2).

The above two processes will be described in detail hereinafter.

Process 1

The reaction of the process 1 is diagramatically shown by the following reaction scheme:

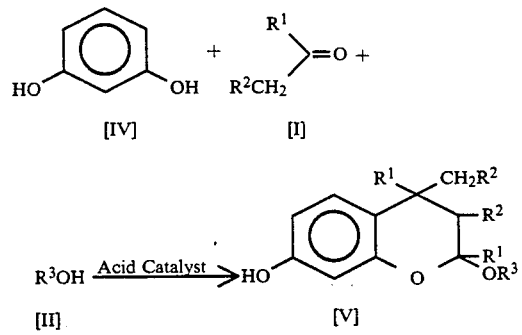

Suitable acid catalysts which may be mentioned include inorganic acids such as hydrochloric acid, sulfuric acid, etc.; organic acids such as methanesulfonic acid, trifluoroacetic acid, etc.; cation exchange resins such as Amberlist 15; solid acids such as phosphomolybdic acid, phosphotungstic acid, etc.; Lewis acids such as cupric chloride, cupric bromide, etc.; trityl hexafluorophosphate; trityl pentachlorostannate; and the like.

Among them, hydrochloric acid, sulfuric acid, methanesulfonic acid and cupric chloride are particularly preferred.

The amount of the acid catalyst used in the present process is in the range of 0.01 to 2 mol, preferably 0.1 to 0.8 mol per mol of resorcin (IV). The amount of aliphatic ketone (I) is in the range of 0.5 to 10 mol, preferably 1 to 5 mol per mol of resorcin. The amount of the alcohol (II) is in the range of 1 to 100 mol, preferably 5 to 40 mol per mol of resorcin. The process may be carried out either in the presence of an inert solvent or without any solvent.

Preferable inert solvents include aromatic hydrocarbons such as benzene, toluene, xylene, etc.; halogenated hydrocarbons such as carbon tetrachloride, 1,2-dichloroethane, etc.; ethers such as isopropyl ether, n-butyl ether, etc.; and the like. These solvents may be used alone or in combinations thereof.

The amount of the solvent used is in the range of 1 to 100 times, preferably, 4 to 70 times the weight of resorcin. The reaction temperature ranges normally from 25° to 160° C. and preferably 70° to 130° C. The reaction may be performed normally for 0.1 to 50 hours, preferably 0.5 to 20 hours.

After the reaction has terminated, the reaction mixture is worked up in conventional manner such as extraction, distillation, chromatography, and the like to give the desired product (V).

The reaction of the process 2 is diagramatically shown by the following reaction scheme:

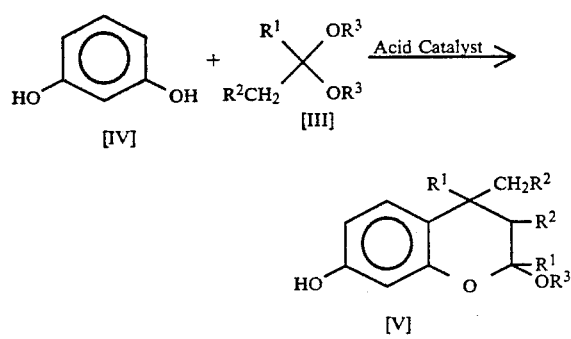

Acid catalysts suitable for this process are the same as those mentioned for the above process 1, and hydrochloric acid, sulfuric acid, methanesulfonic acid and cupric chloride are particularly preferred.

The amount of the acid catalyst is in the range of 0.01 to 2 mol, preferably 0.1 to 0.8 mol per mol of resorcin (IV). The amount of aliphatic ketone acetal (III) is in the range of 0.5 to 5 mol, preferably 1 to 3 mol per mol of resorcin.

The process may be carried out either in the presence of an inert solvent or without any solvent.

The same inert solvents as described in the process 1 may be used in the process 2. In addition, certain alcohols such as methanol, ethanol, etc., may also be used in the process 2.

These solvents may be used alone or in combinations thereof.

The amount of the solvent used is in the range of 1 to 100 times, preferably 2 to 70 times the weight of resorcin.

The reaction temperature, the reaction time, and the method of recovering the desired product (V) are substantially the same as in the process 1.

As mentioned above, there is provided an easy and single-step process for preparing polyalkyl-2-alkoxy-7-hydroxychroman derivatives having two alkyl substituents on the 4-carbon atom of the chroman ring. These compounds are useful as an intermediate for the preparation of agricultural chemicals.

The invention is illustrated, but in no way limited, by the following Examples.

EXAMPLE 1

30 ml glass autoclave was charged with 2.2 g (20 mmol) of resorcin, 2.32 g (40 mmol) of acetone, 3.2 g (100 mmol) of methanol, 0.2 g (2 mmol) of conc. sulfuric acid and 10 ml of toluene, then sealed, and allowed to react at 70° C. for 4 hours. Then, the reaction mixture was cooled to room temperature, neutralized with saturated NaHCO$_3$, washed with water, and toluene was distilled off under reduced pressure. The residue was purified by column chromatography on silicagel using hexane-ethyl acetate as an eluent to give 0.75 g (17.0%) of 7-hydroxy-2-methoxy-2,4,4-trimethylchroman as a colorless oil.

EXAMPLES 2-9

The procedure of Example 1 was repeated except that respective acid catalysts as indicated in Table 1 were used instead of conc. sulfuric acid. The results are shown in Table 1.

TABLE 1

| Example No. | Acid Catalyst | Yield(%) |
|---|---|---|
| 2 | HCl | 17.3 |
| 3 | CF$_3$COOH | 4.1 |
| 4 | CH$_3$SO$_3$H | 15.2 |
| 5 | Amberlist 15 | 4.1 |
| 6 | Phosphotungstic Acid | 17.6 |
| 7 | CuCl$_2$ | 19.0 |
| 8 | CuBr$_2$ | 13.2 |
| 9 | Ph$_3$CSnCl$_5$ | 12.0 |

EXAMPLES 10-12

The procedure of Example 1 was repeated except that respective solvents as indicated in Table 2 were used instead of toluene. The results are shown in Table 2.

TABLE 2

| Example No. | Solvent | Yield(%) |
|---|---|---|
| 10 | 1,2-Dichloroethane | 16.0 |
| 11 | Isopropyl Ether | 4.0 |
| 12 | None | 8.8 |

EXAMPLES 13-18

The procedure of Example 1 was repeated except that varying amounts of sulfuric acid and varying periods of reaction time as indicated in Table 3 were employed. The results are shown in Table 3.

TABLE 3

| Example No. | conc. Sulfuric Acid (mmol) | Reaction Time (hr.) | Yield(%) |
|---|---|---|---|
| 13 | 1.0 | 4 | 20.6 |
| 14 | 2.0 | 4 | 17.0 |
| 15 | 2.0 | 6 | 19.4 |
| 16 | 2.0 | 10 | 19.9 |
| 17 | 2.0 | 20 | 21.2 |
| 18 | 4.0 | 4 | 14.6 |

EXAMPLES 19-41

The procedure of Example 1 was repeated except that varying amounts each of sulfuric acid, acetone, methanol, and toluene and varying reaction temperatures as indicated in Table 4 were employed. The results are shown in Table 4.

TABLE 4

| Example No. | conc. Sulfuric Acid (mmol) | Acetone (mmol) | Methanol (mmol) | Toluene (ml) | Temp. (°C.) | Yield (%) |
|---|---|---|---|---|---|---|
| 19 | 1.0 | 20 | 100 | 10 | 100 | 17.7 |
| 20 | 1.0 | 20 | 200 | 10 | 100 | 21.7 |
| 21 | 1.0 | 40 | 50 | 10 | 100 | 18.7 |
| 22 | 1.0 | 40 | 100 | 10 | 100 | 26.6 |

TABLE 4-continued

| Example No. | conc. Sulfuric Acid (mmol) | Acetone (mmol) | Methanol (mmol) | Toluene (ml) | Temp. (°C.) | Yield (%) |
| --- | --- | --- | --- | --- | --- | --- |
| 23 | 1.0 | 40 | 400 | 10 | 100 | 37.3 |
| 24 | 1.0 | 80 | 100 | 10 | 100 | 28.2 |
| 25 | 1.0 | 80 | 200 | 10 | 100 | 29.2 |
| 26 | 2.0 | 40 | 100 | 60 | 70 | 23.7 |
| 27 | 2.0 | 40 | 100 | 40 | 100 | 32.3 |
| 28 | 2.0 | 40 | 100 | 40 | 130 | 25.0 |
| 29 | 2.0 | 40 | 200 | 10 | 100 | 34.2 |
| 30 | 2.0 | 40 | 200 | 40 | 100 | 40.2 |
| 31 | 2.0 | 60 | 200 | 10 | 100 | 40.9 |
| 32 | 2.0 | 60 | 200 | 30 | 100 | 47.8 |
| 33 | 2.0 | 80 | 200 | 10 | 100 | 41.7 |
| 34 | 2.0 | 80 | 200 | 80 | 100 | 57.0 |
| 35 | 4.0 | 40 | 200 | 80 | 100 | 46.5 |
| 36 | 4.0 | 60 | 200 | 80 | 100 | 56.0 |
| 37 | 4.0 | 60 | 200 | 160 | 100 | 56.8 |
| 38 | 4.0 | 80 | 200 | 80 | 100 | 57.6 |
| 39 | 8.0 | 60 | 200 | 80 | 100 | 59.2 |
| 40 | 8.0 | 80 | 200 | 80 | 100 | 63.3 |
| 41 | 16 | 60 | 200 | 80 | 100 | 50.1 |

EXAMPLE 42

50 ml stainless steel autoclave was charged with 2.2 g (20 mmol) of resorcin, 2.32 g (40 mmol) of acetone, 9.2 g (200 mmol) of ethanol, 0.2 g (2 mmol) of conc. sulfuric acid and 10 ml of toluene, then sealed and allowed to react at 100° C. for 4 hours. Then, the reaction mixture was cooled to room temperature, neutralized with saturated $NaHCO_3$, washed with water, and toluene was distilled off under reduced pressure. The residue was purified by column chromatography on silicagel using hexane-ethyl acetate as an eluent to give 1.01 g (21.4%) of 2-ethoxy-7-hydroxy-2,4,4-trimethylchroman as a colorless viscous liquid.

EXAMPLE 43

30 ml glass autoclave was charged with 2.2 g (20 mmol) of resorcin, 6.2 g (60 mmol) of acetone dimethyl acetal, 6.4 g (200 mmol) of methanol, 0.2 g (2 mmol) of conc. sulfuric acid and 10 ml of toluene, and sealed, and allowed to react at 100° C. for 4 hours. Then, the reaction mixture was cooled to room temperature, neutralized with saturated $NaHCO_3$, washed with water, and toluene was distilled off under reduced pressure. The residue thus obtained was purified by column chromatography on silicagel using hexane-ethyl acetate as an eluent to give 1.26 g (28.3%) of 7-hydroxy-2-methoxy-2,4,4-trimethylchroman as a colorless oil.

EXAMPLE 44

The procedure of Example 43 was repeated except that 0.27 g (2 mmol) of $CuCl_2$ was used instead of conc. sulfuric acid. After similar working up as in Example 43, the desired product was obtained. Yield: 24.2%

EXAMPLES 45-47

The procedure of Example 43 was repeated except that respective solvents as indicated in Table 5 were used instead of toluene. The results are shown in Table 5.

TABLE 5

| Example No. | Solvent | Yield(%) |
| --- | --- | --- |
| 45 | 1,2-Dichloroethane | 28.8 |
| 46 | Isopropyl Ether | 22.3 |
| 47 | Methanol | 21.7 |

EXAMPLES 48-51

The procedure of Example 43 was repeated except that varying amounts of sulfuric acid as indicated in Table 6 was employed. The results are shown in Table 6.

TABLE 6

| Example No. | conc. Sulfuric Acid (mmol) | Yield(%) |
| --- | --- | --- |
| 48 | 1.0 | 11.9 |
| 49 | 4.0 | 29.0 |
| 50 | 8.0 | 25.0 |
| 51 | 16 | 21.1 |

EXAMPLES 52-62

The procedure of Example 43 was repeated except that varying amounts each of sulfuric acid, acetone dimethyl acetal, methanol and toluene and varying reaction temperatures as indicated in Table 7 were employed. The results are shown in Table 7.

TABLE 7

| Example No. | conc. Sulfuric Acid (mmol) | Acetone Dimethyl Acetal (mmol) | Methanol (mmol) | Toluene (ml) | Temp. (°C.) | Yield (%) |
| --- | --- | --- | --- | --- | --- | --- |
| 52 | 2.0 | 60 | 0 | 10 | 100 | 22.0 |
| 53 | 2.0 | 60 | 200 | 20 | 100 | 31.0 |
| 54 | 2.0 | 60 | 200 | 40 | 100 | 39.0 |
| 55 | 2.0 | 60 | 200 | 10 | 70 | 14.5 |
| 56 | 2.0 | 30 | 200 | 40 | 100 | 37.6 |
| 57 | 2.0 | 40 | 200 | 20 | 100 | 44.2 |
| 58 | 2.0 | 40 | 200 | 40 | 100 | 57.8 |
| 59 | 2.0 | 40 | 200 | 80 | 100 | 64.0 |
| 60 | 4.0 | 40 | 200 | 40 | 100 | 53.6 |
| 61 | 4.0 | 40 | 200 | 80 | 100 | 65.2 |
| 62 | 4.0 | 60 | 200 | 10 | 130 | 19.4 |

EXAMPLE 63

100 ml stainless steel autoclave was charged with 2.2 g (20 mmol) of resorcin, 5.28 g (40 mmol) of acetone diethyl acetal, 9.2 g (200 mmol) of ethanol, 0.2 g (2 mmol) of conc. sulfuric acid and 40 ml of toluene, then sealed and allowed to react at 100° C. for 3 hours. After similar working up as in Example 45, 2.42 g (51.3%) of 2-ethoxy-7-hydroxy-2,4,4-trimethylchroman was obtained.

What is claimed is:

1. A process for preparing polyalkyl-2-alkoxy-7-hydroxychroman derivative of the general formula (V):

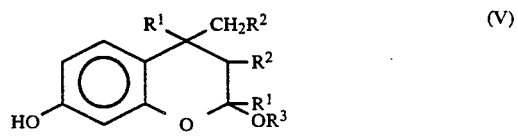

wherein $R^1$ denotes lower primary alkyl, $R^2$ denotes hydrogen or lower primary alkyl and $R^3$ denotes loweralkyl, which comprises reacting resorcin with an aliphatic ketone of the general formula (I):

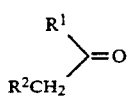 (I)

wherein R¹ and R² are as defined above, and an alcohol of the formula (II):

R³OH (II)

wherein R³ is as defined above, in the presence of an acid catalyst.

2. A process for preparing polyalkyl-2-alkoxy-7-hydroxychroman derivative of the general formula (V):

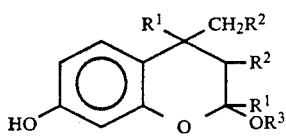 (V)

wherein R¹ denotes lower primary alkyl, R² denotes hydrogen or lower primary alkyl and R³ denotes loweralkyl, which comprises reacting resorcin with an aliphatic ketone acetal of the general formula (III):

wherein R¹, R² and R³ are as defined above, in the presence of an acid catalyst.

3. The process of claim 1, wherein R² is hydrogen.

4. The process of claim 1, wherein R² is lower primary alkyl.

5. The process of claim 1, which comprises reacting the resorcin with 0.5 to 10 mol of the aliphatic ketone (I) and 1 to 100 mol of the alcohol (II) in the presence of 0.01 to 2 mol of the acid catalyst.

6. The process of claim 5, which is carried out in the presence of an inert solvent.

7. The process of claim 5, which is carried out in the absence of a solvent.

8. The process of claim 1, which is carried out at a temperature of from 70° to 130° C. for 0.5 to 20 hours.

9. The process of claim 2, wherein R² denotes hydrogen.

10. The process of claim 2, wherein R² denotes lower primary alkyl.

11. The process of claim 2, which comprises reacting resorcin with 0.5 to 5 mol of the aliphatic ketone acetal (II) in the presence of 0.01 to 2 mol of the acid catalyst.

12. The process of claim 11, which is carried out in the presence of an inert solvent.

13. The process of claim 2, which is carried out at a temperature of from 70° to 130° C. for from about 0.5 to 20 hours.

* * * * *